(12) United States Patent
Bloemenkamp et al.

(10) Patent No.: US 6,465,691 B1
(45) Date of Patent: Oct. 15, 2002

(54) SOLVENT-FREE PROCESS FOR PREPARING THIURAM DISULFIDES

(75) Inventors: Robertus Hermanus Jozef Bloemenkamp, Bathmen (NL); Antonius Johannes van Hengstum, Deventer (NL)

(73) Assignee: Flexsys B.V., Deventer (NL)

( * ) Notice: Subject to any disclaimer, the term of this patent is extended or adjusted under 35 U.S.C. 154(b) by 0 days.

(21) Appl. No.: 09/913,972

(22) PCT Filed: Feb. 15, 2000

(86) PCT No.: PCT/EP00/01256

§ 371 (c)(1),
(2), (4) Date: Oct. 19, 2001

(87) PCT Pub. No.: WO00/50393

PCT Pub. Date: Aug. 31, 2000

(30) Foreign Application Priority Data

Feb. 22, 1999 (EP) .............................................. 99200477

(51) Int. Cl.$^7$ .............................................. C07C 333/32
(52) U.S. Cl. .......................................................... 564/76
(58) Field of Search ........................................... 564/76

(56) References Cited

U.S. PATENT DOCUMENTS 4,459,424 A    7/1984    Eisenhuth et al. ............. 564/76
4,468,526 A    8/1984    Eisenhuth et al. ............. 564/76

OTHER PUBLICATIONS

International Search Report Dated Jul. 29, 1999.

*Primary Examiner*—Peter O'Sullivan
(74) *Attorney, Agent, or Firm*—Louis A. Morris

(57) ABSTRACT

The invention relates to a process for preparing a thiuram disulfide comprising reacting a secondary amine with carbon disulfide in the presence of oxygen and a metal catalyst in the absence of a solvent using a secondary amine of which the corresponding thiuram disulfide is liquid under the reaction conditions. The invention also pertains to the use of said thiuram disulfides as vulcanization accelerators or lubricant oil additives.

9 Claims, No Drawings

SOLVENT-FREE PROCESS FOR PREPARING THIURAM DISULFIDES

This application is a 371 of PCT/EP00/01256, filed Feb. 15, 2000.

The invention relates to a process for preparing thiuram disulfides comprising reacting a secondary amine with carbon disulfide in the presence of oxygen and a metal catalyst.

Such a process is disclosed in U.S. Pat. Nos. 4,468,526 and 4,459,424. The processes that are described in these prior art documents, however, must be performed in a solvent. Typically, methanol is used and in column 5, lines 36–42, of U.S. Pat. No. 4,459,424 it is mentioned that in most cases, as for example with tetramethyl thiuram disulfide, the end product will immediately precipitate out of the reaction mixture and can be filtered off. Alternatively, the products are isolated by means of distillation or extraction from the solvent used.

An obvious disadvantage of using a solvent is that for a process that is to be carried out on an industrial scale, the need of a solvent and the handling thereof add significantly to the cost of the end product. Also, having to use a solvent is a burden on the environment. In addition, fairly large investments need to be made in equipment for separating the product from the solvent used, for example, a solid-liquid separation unit, a liquid-liquid separator (e.g. a centrifuge) when the thiuram disulfide itself is a liquid at room temperature, and a solvent recovery unit.

Surprisingly, we have found a new process which does not suffer from these drawbacks.

The process according to the present invention is characterized in that it is carried out in the absence of a solvent using a secondary amine of which the corresponding thiuram disulfide is liquid under the reaction conditions.

With the invention process thiuram disulfides having good quality can be prepared in at least the same yield as the product which is prepared in a process which employs a solvent. Furthermore, the process is more economical and can be carried out at lower cost, due to the fact that no solvent handling and no investments in equipment for separating the end product from the solvent are required. Also, the reactor capacity is increased, which results in a higher space-time yield.

A wide variety of secondary amines may be used in the process according to the present invention. The only requirement of this amine is that the corresponding thiuram disulfide must be liquid under the reaction conditions, notably the reaction temperature and pressure, of the invention process. The suitability of a secondary amine can be easily checked by running the reaction as described in any one of the Examples described below. The secondary amine which can be used in accordance with the present invention may have the formula $R^1R^2NH$, wherein $R^1$ and $R^2$ are independently selected from linear or branched, saturated or unsaturated $C_2$–$C_{24}$ alkyl groups, $C_3$–$C_{24}$ cycloalkyl groups, $C_6$–$C_{24}$ aryl groups, $C_7$–$C_{24}$ alkaryl groups, and $C_7$–$C_{24}$ aralkyl groups. Hence, the thiuram disulfides which result from reacting $R^1R^2NH$ under the reaction conditions of the process according to the present invention have the formula: $R^1R^2NC(S)SSC(S)NR^1R^2$.

Preferably, $R^1$ and $R^2$ are independently selected from linear or branched, saturated or unsaturated $C_2$–$C_{24}$ alkyl groups.

The process according to the present invention typically is carried out at temperatures in the range of room temperature (i.e. about 20° C.) to 90° C., preferably 45° C. to 75° C., more preferably 50° C. to 70° C. For economic and safety reasons, the reaction ordinarily will not be carried out below room temperature or above 90° C.

The invention process is carried out in the presence of oxygen. Either oxygen gas or a gas containing oxygen, such as air, can be used. The invention process is carried out under pressure. Typically, the process is carried out at oxygen pressures or partial oxygen pressures of at least $0.1 \times 10^5$ Pa (i.e. 0.1 bar), preferably $0.5 \times 10^5$ to $4 \times 10^5$ Pa, more preferably $1.5 \times 10^5$ to $3 \times 10^5$ Pa. As expected, the reaction rate increases with rising oxygen pressure. Due to the fact that the process is carried out under pressure, the reaction typically is carried out in an autoclave suitably equipped with a pressure indicator and a thermometer and, optionally, a mixing device and/or a distillation unit.

The reaction time depends on the process conditions and may range from a few minutes to a few hours under the preferred reaction temperature and partial oxygen pressure conditions. On the reaction scale which is described in the Examples, the reaction typically is stopped when the oxygen flow falls below 1.0 ml/min.

Either a single secondary amine or a mixture of secondary amines can be used in the invention process. Preferably, $R^1$ and $R^2$ are the same. When a single secondary amine is used as reactant, a thiuram disulfide carrying the same substituents on both nitrogen atoms is obtained. In the case of a symmetrically substituted secondary amine being used, a thiuram disulfide with four identical substituents is obtained. When two different secondary amines are used as reactants, depending on the process conditions such as differences in the basicity of the amines and/or molar ratios, thiuram disulfides with two differently substituted nitrogen atoms are obtained.

Typical examples of aliphatic, cycloaliphatic, aromatic, alkaromatic, and aralyphatic secondary amines which can be used in the process of the present invention may be selected from the ones that are listed in column 3, line 35, through column 4, line 36, of U.S. Pat. No. 4,459,424.

Preferred secondary amines are diethylamine, dibutylamine, dioctylamine, ditallowamine, and dicocoamine.

In the invention process, the amount of secondary amine relative to carbon disulfide may be varied. Preferably, about equimolar amounts of the secondary amine and carbon disulfide are used. In order to allow all of the secondary amine to react, it may also be practical to use a slight excess of carbon disulfide, i.e. 2–10 mole %. After completion of the reaction said slight excess of carbon disulfide can easily be removed from the reaction mixture by evaporation.

Typical examples of metal catalysts which can be used in the process of the present invention include the catalysts that are described in column 2, line 50, through column 3, line 26, of U.S. Pat. No. 4,459,424.

Preferred catalysts are those based on manganese or copper. A particularly preferred manganese catalyst is manganese acetate.

The amount of catalyst to be used in the invention process can be small. Typically, an amount of 0.01 to 5 mmoles of catalyst per mole of secondary amine is used. Preferably, an amount of 0.05 to 2.5 mmoles of catalyst per mole of secondary amine is used.

The process of the present invention is optionally carried out in the presence of a co-catalyst, typically a tertiary amine. Suitable tertiary amines include the ones listed in column 3, lines 34–41, of U.S. Pat. No. 4,468,526.

The process may be carried out in various ways as, for example, described in column 5, lines 1–21, of U.S. Pat. No. 4,459,424. It is preferred to perform the reaction by dosing such an amount of carbon disulfide to a mixture of the secondary amine (about 0.5 mole based on 1 mole of secondary amine) and metal catalyst that the corresponding ammonium dithiocarbamate is formed, followed by the introduction of oxygen or an oxygen-containing gas and further dosing of carbon disulfide in such a way that the partial pressure of carbon disulfide is kept as low as possible.

Depending on the secondary amine which has been used as the starting material for preparing the thiuram disulfide in accordance with the process of the instant invention, the product is isolated by cooling the reaction mixture in the case of a thiuram disulfide which is liquid at room temperature or by extruding or pelletizing the reaction mixture in the case of a thiuram disulfide which is solid at room temperature Suitable equipment for extrusion and pelletization of the warm reaction mixture is known to the person skilled in the art.

Typically, the metal catalyst and any co-catalyst which may have been used in the invention process is left in the product without having deleterious effects in applications where the thiuram disulfides are used. If desired, however, the catalysts can be removed by washing with an aqueous acidic solution. For example, hydrochloric acid may be used for this purpose.

The process of the invention can be carried out as a batch or continuous process and can be performed on a small or industrial scale. Typically, the invention process is performed batch-wise.

The invention also relates to the use of thiuram disulfides prepared in accordance with the invention process as vulcanization accelerators for synthetic and natural rubbers and additives for lubricant (lube) oils. Thiuram disulfides prepared from secondary amines having linear $C_2$–$C_7$ alkyl groups are particularly suitable as vulcanization accelerators, whereas thiuram disulfides derived from secondary amines containing saturated or unsaturated $C_8$–$C_{24}$ alkyl groups are suitable as lubricant oil additives.

The invention is illustrated by the following examples.

Experimental

Materials

Diethylamine, ex Baker

Dibutylamine, ex Baker

Dioctylamine, ex Acros

Dicocoamine (Armeen® 2C), ex Akzo Nobel

Carbon disulfide ($CS_2$), ex Baker

Manganese acetate ($Mn(OAc)_2 4H_2O$), ex Fluka

For the determination of the thiuram disulfide content, a sample of the product is reduced with hydrogen sulfide ($H_2S$) and the amine formed is titrated with an aqueous hydrochloric acid solution.

EXAMPLE 1

Liquid dicocoamine (320 g) containing 90.6 wt % secondary amine (0.76 mole) at 70° C. was charged into a 1-liter autoclave equipped with a turbine stirrer which was preheated to 50° C. The manganese acetate catalyst (96 mg, 0.39 mmole) was added to the reactor as a powder. The reactor was closed and evacuated to a pressure of $0.18 \times 10^5$ Pa (0.18 bar). Carbon disulfide (33 g, 0.43 mole) was dosed within 20 minutes with stirring at 300 rpm and the temperature of the reaction mixture was kept at 55° C. The reactor was pressurized to $1.56 \times 10^5$ Pa (1.56 bar) with pure oxygen and the stirring speed was increased to 1400 rpm. Carbon disulfide dosing was started again at a dosing speed of 0.5 g/min and the reaction was finished after 65 min when the oxygen flow was lower than 1.0 ml/min and oxygen uptake was considered to be complete. A total of 61.5 g of carbon disulfide was dosed. The reaction mixture was removed from the reactor at 55° C. and the product was dried at 70° C./$50 \times 10^2$ Pa (50 mbar) for 1 h. Yield: 378.8 g of a light brown oil containing 84% by weight of tetracoco thiuram disulfide (as determined by NMR).

The space-time yield was calculated to be 746 g of product per kg of reaction mixture per hour.

Comparative Example A

Liquid dicocoamine (159 g) containing 90.6 wt % secondary amine (0.38 mole) at 70° C. was charged into a 1-liter autoclave equipped with a turbine stirrer. Methanol (330 g) and water (16 g) were added to the autoclave together with manganese acetate (96 mg, 0.39 mmole). Carbon disulfide (33.5 g, 0.44 mole) was dosed and the oxidation reaction was carried out at 55° C. and an oxygen pressure of $0.56 \times 10^5$ Pa. After 4 h, the oxygen flow fell below 1 ml/min and the reaction mixture was removed from the reactor. The solvent was removed and the reaction product was dried at 70° C./$50 \times 10^2$ Pa for 2 h. Yield: 180.6 g of a light brown oil containing 84% by weight of tetracoco thiuram disulfide (as determined by NMR).

The space-time yield was calculated to be 84 g of product per kg reaction mixture per hour.

The solvent-free process in accordance with the present invention requires less catalyst and results in a higher space-time yield than the solvent process of the prior art, c.f. the data for the preparation of tetracoco thiuram disulfide of Example 1 and Comparative Example A.

EXAMPLE 2

Tetracoco thiuram disulfide was also prepared on a 60-liter scale. Liquid dicocoamine (19.3 kg) containing 90.6 wt % secondary amine (45.8 moles) at 70° C. was charged into the 60-liter autoclave equipped with a turbine stirrer. Then, manganese acetate (23.3 g, 0.095 mole) was added to the reactor as a 25 wt % slurry in water. The reactor was evacuated to a pressure of $0.1 \times 10^5$ Pa (0.1 bar). Carbon disulfide (2.2 kg, 28.9 moles) was dosed within 15 min with stirring and the temperature of the reaction mixture was maintained at 60° C. The reactor was pressurized to $1.55 \times 10^5$ Pa (1.55 bar) with pure oxygen and the stirring speed was increased (power input 4 kW/m$^3$) to start the oxidation reaction. Carbon disulfide dosing was started again and the remaining quantity of $CS_2$ was dosed within 75 min. A total of 3.7 kg of carbon disulfide (48.7 moles) was dosed. Oxygen was added to maintain total pressure at a level of $1.55 \times 10^5$ Pa. After 2 h, oxygen consumption was lower than 1.0 ml/min and the reaction was considered to be complete. The reaction mixture was stirred for another 30 min and then stripped with nitrogen at 60° C./$0.3 \times 10^5$ Pa (300 mbar) (yield:22.7 kg of a light brown oil containing 84 wt % of tetracoco thiuram disulfide (as determined by NMR)).

EXAMPLE 3

Following the same procedure as described in Example 1, except that the total pressure was $3 \times 10^5$ Pa (3 bar) and the reaction time was 90 min, dioctylamine was converted into tetraoctyl thiuram disulfide in 99% yield (product purity: 97.5% by weight as determined by NMR).

EXAMPLE 4

Following the same procedure as described in Example 1, except that the total pressure was $3 \times 10^5$ Pa (3 bar) and the reaction time was 120 min, dibutylamine was converted into tetrabutyl thiuram disulfide in quantitative yield (product purity: 98% by weight according to NMR and 96.3% by weight according to the $H_2S$ titration method).

EXAMPLE 5

Diethylamine (150 g, 2.05 moles) and manganese acetate catalyst (30 mg, 0.12 mmole) were charged into a 1 liter reactor at room temperature. The reactor was evacuated to $0.6 \times 10^5$ Pa (0.6 bar) and carbon disulfide (87.5 g, 1.15 moles) was dosed in 20 min while increasing the temperature to 60° C. The reactor was pressurized to $3 \times 10^5$ (3 bar) with pure oxygen and the stirring speed was raised to 1400 rpm. Carbon disulfide dosing was started again at a dosing rate of 2 moles per mole oxygen reacted, i.e. 68.5 g (0.90 mole) in 280 min. The reaction was stopped when the oxygen flow fell below 1 ml/min. After removal of the reaction water formed by evaporation, 295 g of tetraethyl thiuram disulfide were obtained (yield: 97.2 wt %) with a purity of 96.7 wt % (as determine d by the $H_2S$ titration method).

The space-time yield was calculated to be 160 g of product per kg of reaction mixture per hour.

It was found that at a higher reaction temperature of 75° C., the reaction time decreased, but the active content of the product decreased as well.

Comparative Example B

Methanol (270 g) and water (30 g) were added to the 1-liter autoclave. Manganese acetate (68 mg, 0.277 mmole) was added as a powder and the reactor was evacuated to $0.3 \times 10^5$ Pa (0.3 bar). The temperature was increased to 50° C. and the pressure was increased with pure oxygen to $1.56 \times 10^5$ Pa. The stirring speed was increased from 200 to 1400 rpm and 50.2 g of $CS_2$ (0.66 mole) and 48.3 g of diethyl amine (0.66 mole) were both dosed over a period of 90 min, oxygen being added to maintain the total pressure at a level of $1.56 \times 10^5$ Pa. After 180 min, oxygen consumption was less than 1 ml/min and the reaction was considered to be complete. The mixture was cooled to 7° C. and the precipitated product was recovered by filtration in a yield of 88 wt % (86 g of diethyl thiuram disulfide) with a purity of 99.0 wt % (as determined by the $H_2S$ titration method).

The space-time yield was calculated to be 70 g of product per kg of reaction mixture per hour.

The solvent-free process in accordance with the present invention requires less catalyst and results in a higher space-time yield than the solvent process of the prior art, c.f. the data for the preparation of tetraethyl thiuram disulfide of Example 5 and Comparative Example B.

What is claimed is:

1. A process for preparing a thiuram disulfide comprising reacting a secondary amine with carbon disulfide in the presence of oxygen and a metal catalyst, said process being carried out in the absence of a solvent using a secondary amine selected so that the corresponding thiuram disulfide is liquid under the reaction conditions.

2. The process of claim 1 wherein the reaction temperature is in the range of room temperature to 90° C. and the oxygen pressure or partial oxygen pressure is at least $0.1 \times 10^5$ Pa.

3. The process of claim 1 wherein the secondary amine has the formula $R^1R^2NH$, wherein $R^1$ and $R^2$ are independently selected from linear or branched, saturated or unsaturated $C_2$–$C_{24}$ alkyl groups, $C_3$–$C_{24}$ cycloalkyl groups, $C_6$–$C_{24}$ aryl groups, $C_7$–$C_{24}$ alkaryl groups, and $C_7$–$C_{24}$ aralkyl groups.

4. The process of claim 3 wherein $R^1$ and $R^2$ are independently selected from linear or branched, saturated or unsaturated $C_2$–$C_{24}$ alkyl groups.

5. The process of claim 3 wherein $R^1$ and $R^2$ are the same.

6. The process of claim 1 wherein the secondary amine is selected from the group consisting of diethylamine, dibutylamine, dioctylamine, ditallowamine, and dicocoamine.

7. The process of of claim 1 wherein about equimolar amounts of the secondary amine and carbon disulfide are used.

8. The process of claim 1 wherein from 0.05 to 2.5 mmoles of metal catalyst per mole of secondary amine is used.

9. The process of claim 1 wherein the metal catalyst is a manganese or copper catalyst, preferably manganese acetate.

\* \* \* \* \*